United States Patent
Maier-Hein et al.

(10) Patent No.: US 9,498,132 B2
(45) Date of Patent: Nov. 22, 2016

(54) VISUALIZATION OF ANATOMICAL DATA BY AUGMENTED REALITY

(71) Applicant: Deutsches Krebsforschungszentrum Stiftung des öffentlichen Rechts, Heidelberg (DE)

(72) Inventors: Lena Maier-Hein, Heidelberg (DE); Markus Fangerau, Leimen (DE); Hans-Peter Meinzer, Heidelberg (DE); Alexander Seitel, Heidelberg (DE)

(73) Assignee: Deutsches Krebsforschungszentrum Stiftung des öffentlichen Rechts, Heidelberg (DE)

( * ) Notice: Subject to any disclaimer, the term of this patent is extended or adjusted under 35 U.S.C. 154(b) by 667 days.

(21) Appl. No.: 13/891,310

(22) Filed: May 10, 2013

(65) Prior Publication Data

US 2013/0245461 A1  Sep. 19, 2013

Related U.S. Application Data

(63) Continuation of application No. PCT/EP2011/005735, filed on Nov. 14, 2011.

(30) Foreign Application Priority Data

Nov. 12, 2010 (EP) .................................. 10191085

(51) Int. Cl.
*A61B 5/00* (2006.01)
*A61B 6/00* (2006.01)

(52) U.S. Cl.
CPC ........... *A61B 5/0035* (2013.01); *A61B 5/0077* (2013.01); *A61B 5/742* (2013.01); *A61B 34/10* (2016.02); *A61B 34/20* (2016.02);

(Continued)

(58) Field of Classification Search
CPC .............. A61B 2019/5289; A61B 2019/5297; A61B 2019/5291
USPC ......................................................... 600/476
See application file for complete search history.

(56) References Cited

U.S. PATENT DOCUMENTS

| | | | | |
|---|---|---|---|---|
| 7,787,927 B2* | 8/2010 | Wood | ..................... | A61B 6/032 378/20 |
| 2003/0114741 A1* | 6/2003 | Vilsmeier | ................ | A61B 6/00 600/407 |
| 2004/0263535 A1 | 12/2004 | Birkenbach | .................. | 345/629 |
| 2007/0086678 A1* | 4/2007 | Chefd'hotel | ......... | G06K 9/6289 382/294 |

(Continued)

OTHER PUBLICATIONS

European Patent Office, International Search Report, PCT/EP2011/005735, date of mailing Mar. 5, 2012, 9 pages.

*Primary Examiner* — Rajeev Siripurapu
(74) *Attorney, Agent, or Firm* — Sunstein Kann Murphy & Timbers LLP

(57) ABSTRACT

A sensor means is employed to sense a distance to the surface of a subject to be examined, so that a range image may be acquired. Intensity information may be acquired alongside the distance information. The distance information and intensity information may be evaluated to track the pose of the sensor means relative to the surface of the subject to be examined, so that anatomical data related to said subject may be displayed as seen from the position and/or orientation of the sensor means or display means. By moving the sensor means or display means along the surface of the subject to be examined, such as a patient in a hospital environment, the user hence gets the impression of being able to look directly into the human body.

22 Claims, 3 Drawing Sheets

Figure 1a

(52) U.S. Cl.
CPC ............ *A61B 90/361* (2016.02); *A61B 6/462* (2013.01); *A61B 6/5223* (2013.01); *A61B 6/5235* (2013.01); *A61B 2034/105* (2016.02); *A61B 2034/2065* (2016.02); *A61B 2090/061* (2016.02); *A61B 2090/365* (2016.02); *A61B 2090/372* (2016.02)

(56) References Cited

U.S. PATENT DOCUMENTS

| | | | |
|---|---|---|---|
| 2010/0039506 A1 | 2/2010 | Sarvestani | 348/65 |
| 2010/0114265 A1 | 5/2010 | Lechthaler | 607/94 |
| 2012/0143049 A1* | 6/2012 | Neubauer | A61B 19/5244 600/424 |

* cited by examiner

VISUALIZATION OF ANATOMICAL DATA BY AUGMENTED REALITY

This application is a continuation of co-pending Patent Cooperation Treaty PCT/EP2011/005735, filed Nov. 14, 2011, which in turn claims priority from European Patent Application 10191085.9, filed Nov. 12, 2010, which are incorporated herein by reference.

TECHNICAL FIELD

The present invention relates to a system and method for visualizing anatomical data, in particular to a system and method for mobile augmented reality for on-patient visualization of pre-recorded medical images and to a system and method for assisting in image-guided interventions.

BACKGROUND ART

Visualization of anatomical data for disease diagnosis, surgical planning, or orientation during interventional therapy is an integral part of modern health care. However, only few medical imaging modalities are capable of providing real-time images of the patient's anatomy. A common procedure therefore involves the acquisition of static three-dimensional images, e.g. by means of computed tomography (CT) or magnetic resonance imaging (MRI) scanners, and subsequently manipulating and visualizing the acquired data on a computer, or radiological workstation.

For example, the data acquired from the CT or MRI scan of a patient's head may be used to generate a three-dimensional virtual model of the head and to display different views of the model. The computer may seemingly rotate the 3D virtual model of the head so that it can be seen from different angles, or may remove parts of the model so that hidden parts become visible, e.g. remove a part of the skull to inspect a tumor hidden underneath, or may highlight certain parts of the head such as soft tissue, so that those parts become more visible. Such techniques can assist a surgeon to decide upon the best point or direction from where to enter a patient's head to remove a tumor so as to minimize damage to the surrounding structure. They may also prove helpful for anatomy teaching.

However, in such conventional techniques it is usually the task of the physician to mentally transfer the three-dimensional virtual image to the patient, or in other words to establish a correspondence between the real object and the 3D virtual image generated from the static medical data. This not only requires considerable skill and experience, but is also prone to failures, which might have very serious consequences for the patient under therapy. In addition, navigation in the three-dimensional data set may not be as intuitive as desired and is often rather cumbersome. The inventors have repeatedly made the experience that surgeons sometimes require considerable time and training to get acquainted to new visualization software, and to find out which body part of the patient is currently displayed, or how to move to a different body part of the patient.

A system and method for mapping a three-dimensional virtual model of a body part to the real object is disclosed in United States Patent Application US2007/0018975 A1. The model is displayed on a computer screen and superimposed with an image of the real object taken by means of a video camera. The pose of the video camera in real space and/or the orientation of the 3D virtual object are varied until the virtual image is perfectly aligned with the real image. The pose of the camera in a real space may be tracked, and the orientation of the 3D virtual model may then be changed to follow the movement of the video camera. This can enable a physician to view subsurface structures from a perspective that corresponds to the current position or orientation of the video camera. The effect is a kind of "x-ray vision", which allows the surgeon to see below the surface and into the patient. This may help the surgeon to operate on the patient with enhanced precision, and without having to mentally transfer the 3D virtual images shown on the computer screen to the patient placed before him.

However, the system disclosed in US2007/0018975 A1 requires means adapted to track the pose of the camera in real space, and hence can only be employed in specially equipped environments, e.g. in a specially equipped operating theatre. It further requires a careful initialization to guarantee that the coordinate system of the virtual 3D image is in perfect alignment with the coordinate system of the camera moving in real space. Only then does the view of the 3D virtual model correspond exactly to the orientation of the camera in real space. In addition, the patient is not allowed to move during inspection, for otherwise the coincidence of the coordinate system of the virtual model with the coordinate system of the camera in real space may be lost.

SUMMARY

It is hence the objective of the present invention to provide an improved system and method for visualizing anatomical data that avoids a lengthy initialization and provides enhanced user flexibility.

This objective is achieved by a system for visualizing anatomical data with the features of claim 1, and a corresponding method for visualizing anatomical data with the features of claim 12. The dependent claims relate to preferred embodiments.

A system for visualizing anatomical data according to the present invention comprises a display means, a sensor means adapted to sense a distance of said sensor means to at least a part of a surface of subject to be examined, and a position tracking means adapted to determine a position and/or an orientation of said sensor means, and/or a position and/or orientation of said display means relative to said surface of said subject by evaluating distance information provided by said sensor means. The system further comprises a visualization means adapted to visualize on said display means information generated from anatomical data relating to said subject, wherein said visualization means is adapted to visualize said information generated from said anatomical data on said display means in accordance with said position and/or orientation of said sensor means, and/or in accordance with said position and/or orientation of said display means.

In the present invention, the position and/or orientation of the sensor means relative to the surface of the subject to be examined may be determined directly by sensing the distance of said sensor means to said surface. Hence, no additional tracking equipment other than the sensor means is required. Thus, the system according to the present invention is ready to use, and does not require a specifically equipped environment. As a result, the use of the present invention is not limited to specifically equipped operating theatres, treatment rooms, or lecture halls. Rather, the system according to the present invention may be used wherever the subject to be examined is located, either in a hospital, in a doctor's surgery, in a lecture hall, or even at home or outdoors. This significantly enhanced the versatility of on-patient visualization of medical images and on-patient anatomy teaching.

Moreover, the system according to the present invention does not require a time-consuming initialization. Since the position of the sensor means relative to the subject to be examined is determined directly by evaluating the distance of the sensor means to at least a part of the surface of the subject, the subject is not required to remain in a fixed and static position. Hence, the patient may move during the examination or inspection.

A subject in the sense of the present invention may be a patient to be examined. In this case, the anatomical data relating to said patient may be pre-recorded medical image data of said patient, for instance image data generated from raw data acquired during a CT scan or a MRI scan. Alternatively or additionally, said anatomical data may comprise generic data not previously acquired from the patient to be examined, but collected from a generic database, such as an anatomical atlas.

The subject to be examined may also be a model, such as a doll of a human being or animal, in particular in applications to anatomy teaching. In this case, said anatomical data may comprise medical data collected from an anatomical atlas, or prepared by an instructor. The subject under examination may also be a skeleton, such as the skeleton of a human being or animal. In more generality, a subject in a sense of the present invention may be any object, alive, dead, or artificial, that comprises anatomical structures, or can serve as a model for an object comprising anatomical structures.

Said surface may be any surface that can be sensed by means of said sensor means, such as an outer surface of said subject or a surface of an organ of a patient undergoing open surgery.

Anatomical data in the sense of the present invention may comprise medical image data, for instance image data gathered from a CT or MRI scan of a patient to be examined. Anatomical data may further comprise data pertaining to, or representing an anatomical structure, such as a body part. Such data may be gathered directly from the subject under investigation, or may be generated from a medical atlas or database. Anatomical data may also comprise medical labels, such as labels displayed on said display means to denote or point to anatomical structures. Said anatomical data may also comprise drawings or images of anatomical abnormalities.

Information generated from anatomical data may comprise a proposed or predetermined insertion path into or through the subject, for instance a path suggested for a needle insertion into a patient. Generally speaking, information generated from anatomical data in the sense of the present invention may be any data that is derived from, relates to or describes anatomical structures of said subject to be examined.

By sensing a distance of said sensor means to a plurality of points on the surface of the subject, where not all of these points lie on a common line, the position and/or orientation of the sensor means relative to the surface may be reliably evaluated. Movements of the subject may be taken into account by frequently updating the distance measurements.

Preferably, said sensor means is adapted to acquire a range image of at least part of a surface of said subject to be examined. This may be achieved by evaluating the distance of said sensor means to a plurality of points on the surface of the subject to be examined. Preferably, said sensor means may also be adapted to acquire intensity information alongside said distance information.

In a preferred embodiment, said sensor means is portable. This allows to move the sensor means freely along the body of the subject under investigation, and to register the range data acquired by evaluating the distance information and/or intensity information with said anatomical data, for instance with anatomical labels, supplementary anatomical information, or 3D medical image data. The user may hence obtain a kind of "x-ray vision" into a patient from a perspective that corresponds to the current position and/or orientation of the portable sensor means or, in other words, a view into the patient as seen from the position and/or orientation of the portable sensor means.

Since navigation through the three-dimensional data set is performed directly at the patient, it becomes more intuitive and requires less user experience.

According to a preferred embodiment, said display means is likewise portable and is attached to said sensor means. The display means may thus be moved along the subject to be examined together with the sensor means, which allows the user to directly look at the subject to be examined through the display means, or even provides him with the impression of being able to look directly into the subject to be examined, such as a patient under surgery. A system according to this preferred embodiment is particularly easy and intuitive to use, and is very suitable for anatomy teaching directly at the patient.

In a preferred embodiment, said sensor means may be further adapted to sense a distance of said sensor means to said display means. This may allow the sensor means to remain fixed, whereas the display means may be portable and may be moved along the subject to be examined. The position and/or orientation of the display means relative to the surface of the subject may be tracked by continuously evaluating the distance between said sensor means and said display means. Based on the distance information of the sensor means relative to both the surface of the subject to be examined and the display means, anatomical data may be displayed on said display means in accordance with said position and/or orientation of said display means with respect to said surface of said subject.

According to a preferred embodiment, said sensor means may comprise a time-of-flight camera (ToF camera). A time-of-flight camera is a camera system that creates a range image by evaluating the distance between the camera device and the objects in the camera range, and may additionally provide intensity information on the objects in the camera range. It is an advantage of time-of-flight cameras over conventional laser scanners that a whole scene may be captured at once. State of the art cameras may provide more than 50 frames per second.

Alternatively or additionally, said sensor means may comprise a conventional (colour or black and white) optical camera. Said optical camera may be adapted to provide an intensity image, as an example.

Said sensor means may sense said distance of said sensor to said surface of said subject by employing stereoscopy, structured light, passive monocular techniques and/or simultaneous localization and mapping (SLAM).

Image recognition techniques may be employed to identify and track image features in consecutive images provided by said optical camera to account for updates whenever the position and/or orientation of said sensor means relative to said surface is changed. Camera-based methods for 3D surface reconstruction and/or feature tracking, such as stereoscopy or structure for motion may be applied to generate information about said surface. This data may be combined with the data acquired from a time-of-flight camera to provide an improved estimate of the current camera position and/or orientation.

Images from several consecutive frames may be combined into a single image to obtain more information on the surface, and/or to generate a bigger surface image.

Said display means may comprise a flat screen, a notebook screen, or a tablet computer screen. It may also comprise a head-mounted display, or any 3D display.

Said visualization means may be adapted to visualize said anatomical data at a position on said display means in accordance with a position of an anatomical feature of said subject to be examined as seen from a direction and/or from a distance that correspond to a direction and/or a distance between said subject and said sensor means, or a direction and/or a distance between said subject and said display means.

Said visualization means is preferably adapted to visualize said anatomical data relating to said object on said display means as seen from direction and/or from a distance but correspond to a direction and/or distance between said subject and said sensor means, or a direction and/or distance between said subject and said display means.

By visualizing the anatomical data from a perspective that corresponds to the perspective of the sensor means with respect to the subject to be examined, the user obtains the impression of looking at the subject from the perspective of the sensor means.

In particular, said visualization means may be adapted to visualize anatomical data relating to an internal structure of said subject on said display means as seen from a direction and/or from a distance that correspond to a direction and/or a distance between said internal structure of said subject and said sensor means, or a direction and/or a distance between said internal structure of said subject and said display means. Said internal structure may be a body part of a patient.

The perspective may be defined by a direction connecting the sensor means and a part of said surface of said subject, or a direction connecting the sensor means and said body part lying underneath said surface. The perspective may be further defined by a viewing angle of the sensor means with respect to said part of said surface of said subject, or a viewing angle of the sensor means with respect to the body part. The distance at which the surface or body part is displayed on the display means may be indicative of the actual physical distance between the sensor means and the surface or the body part, respectively, or may be proportional to the physical distance, with a proportionality factor to account for scaling, i.e. magnification and diminution according to the needs of the user.

In case the relative arrangement of said sensor means and said display means is known, e.g. if said display means is attached to said sensor means, said body part may also be visualized as seen from the perspective of the display means (such as a screen). This can be achieved by computing the image data from a perspective of the portable sensor means as indicated above, and then correcting for the relative displacement of the display means with respect to the sensor means by calibration. A corresponding effect may be achieved when the sensor means tracks the display means.

Said sensor means may be further adapted to record a physical image of said surface of said subject, and said visualization means may be adapted to displace said surface image together with anatomical data relating to at least a part of said surface, for instance anatomical data relating to an internal structure lying underneath at least a part of said surface.

A physical image in the sense of the latter embodiment may be a real image, for instance an image showing some physical properties of said surface of said subject, e.g. a video image, or a range image or intensity image provided by a time-of-flight camera.

By displaying the surface image together with the anatomical data, a very intuitive visualization can be achieved that may allow the user to inspect both an internal structure of the patient to be examined and its relative arrangement to the surface structure hiding it. This may be particularly helpful for surgical planning, or as an orientation means during interventional therapy. For instance, the visualization means may be adapted to visualize the body part of interest whereas its neighbouring body parts may be masked by the overlying surface structure displayed as the physical image. In this configuration, the image on display may contain both the visualization of (virtual) medical image data and a physical (real) image of the surface of a patient, such as the patient's skin or clothing.

In an embodiment of the invention, said system may be adapted to generate from said distance information and/or from intensity information acquired at a first point in time a first estimate of said position and/or said orientation of said sensor means and/or said display means, for instance by comparing said distance information and/or intensity information against said anatomical data, and may be further adapted to subsequently generate a second (refined) estimate of said position and/or said orientation by evaluating said first estimate and comparing said distance information and/or intensity information against distance information and/or intensity information acquired at a second point in time, said second point in time later than said first point in time.

In a preferred embodiment, the system may be adapted to generate from said distance information a first surface profile of at least a part of said surface of said patient, and further comprises comparison means adapted to compare said first surface profile against a second surface profile generated from said anatomical data, for instance by means of graph matching. For instance, said second surface profile may be generated from pre-recorded medical image data, such as a CT or MRI scan.

Comparison of said first surface profile generated from a range image with said second surface profile generated from the anatomical data allows the system to automatically determine and update the position of the sensor means relative to the surface of said subject to be examined. Hence, the use of markers or time-consuming initialization can be avoided.

In a further preferred embodiment, the system may be adapted to identify a first plurality of landmarks from a range image and a second plurality of landmarks from said anatomical data, and may be further adapted to determine said position and/or orientation of said sensor means and/or to visualize said anatomical data on said display means by matching said first plurality of landmarks to said second plurality of landmarks.

A range image in the sense of the latter embodiment may be a range image provided by a time-of-flight camera providing distance and/or intensity information, or may also comprise a video image.

Identifying a plurality of landmarks in the range image and matching them to corresponding landmarks extracted from the anatomical data, such as virtual medical image data, allows to determine the position of the sensor means and/or display means relative to the surface of said subject with a high degree of accuracy. Landmarks in the sense of the latter embodiment may be any prominent or characteristic features in the surface profile, such as a characteristic curvature corresponding to a joint, or an opening corresponding to an orifice of the subject to be examined. These characteristics may be found both in the range image generated from the distance information and/or intensity information and in the virtual 3D medical image. However, said landmarks may also be prominent or characteristic features in the intensity image or in an optical video image, such as an intensity gradient or colour gradient. Artificial landmarks such as markers, which may be placed along the body of the subject to be examined, may likewise be used, both additionally or alternatively.

Alternatively or additionally, said system may be adapted to generate from said distance information and/or intensity information a skeleton model of said subject, for instance a skeleton model of a patient to be examined, wherein nodes in said skeleton model may represent joints of said patient, and edges in said skeleton model may represent limbs of said patient connecting said joints. Once a skeleton model has been obtained, this may be registered with the anatomical data relating to the subject, for instance with medical image data acquired from a CT or MIR scan.

Said latter embodiments employing graph matching, landmark-based registration, or skeleton-based registration are particularly suited for determining an initial position and/or orientation of said sensor means and/or said display means relative to said surface of said subject. They may be employed as alternatives, or may be likewise employed to complement one another.

According to a preferred embodiment, said system may be further adapted to determine said position and/or orientation of said sensor means by generating a surface profile of at least a part of said surface of said subject from said distance information and/or from intensity information, comparing said surface profile against said anatomical data, and computing an affine transformation that aligns said anatomical data with said surface profile. In particular, a first surface profile may be generated from said distance information and/or intensity information, and a second surface profile may be generated from said anatomical data, for instance from pre-recorded medical image data, and said first surface profile may be compared against said second surface profile to compute an affine transformation that aligns said first surface profile with said second surface profile.

By continuously comparing said first surface profile generated from said distance information and/or intensity information against surface information generated from said anatomical data, a change of position and/or orientation resulting from a movement of the sensor means and/or display means along the subject to be examined may be accounted for, and the display means may be updated such that an internal structure of said subject may be displayed under a different angle or from a different direction or distance that correspond to the current position of the sensor means and/or display means.

Alternatively or additionally, said system may be adapted to determine said position and/or orientation of said sensor means and/or said display means by selecting a plurality of features in a first image generated from said distance information and/or from intensity information, identifying the positions of said features in said first image, and identifying at least a part of said plurality of features and their respective positions in a second image generated from said distance information and/or from intensity information.

A first image in the sense of the latter embodiment may be any image acquired from information provided by the sensor means at some point in time, and a second image in the sense of the latter embodiment may be another image acquired from information provided by the sensor means at a later point in time. The first or second image, respectively may not be limited to information generated from a single frame, but may each comprise information acquired over a plurality of image frames. This may contribute to a more precise registration.

According to the latter embodiment, updating of the display to account for changes in the position and/or orientation of the sensor means and/or display means relative to the surface of the patient may rely on a comparison of physical images provided by the sensor means, e.g. range images, or intensity images, or video images. A plurality of characteristic or prominent features in a first image may be identified, e.g. features characterized by a large gradient or large curvature of a surface profile, or a steep intensity gradient in an intensity image. Such features may serve as landmarks that can be identified in consecutive images taken after the position or orientation of the sensor means and/or display means has been amended. This likewise allows to reliably account for movements of the sensor means and/or display means relative to the surface of said subject to be examined, so that the user is always presented with an image seen from a perspective corresponding to the current position and/or orientation of the sensor means and/or display means.

Additionally or alternatively, said system may also be adapted to determine said position and/or orientation of said sensor means and/or said display means by simulating a first range image based on said anatomical data, and comparing said simulated first range image against a second range image generated from said distance information. In particular, a plurality of first range images may be simulated that correspond to different modifications of a previously determined position and/or orientation of said sensor means and/or said display means, and may be compared against said second range image to identify the simulated range image that best corresponds to the second range image.

According to the latter embodiment, changes in the position and/or orientation of the sensor means may be accounted for by simulating range images on the basis of said anatomical data, for instance on the basis of pre-recorded medical image data. A plurality of parameters indicative of a position and/or orientation of said sensor means may be modified with an evolutionary algorithm, and corresponding range images may be derived, for instance from the surface meshes in the medical image data set. These simulated range images may be compared against the acquired true range image, and the difference may be quantified by means of a cost function. The updated position and/or orientation of the sensor means and/or display means may be determined by identifying those parameters corresponding to the best similarity value.

The latter embodiments are particularly suitable for a fine-grained estimation of the position and/or orientation of said sensor means and/or said display means, once a rough estimation has been provided by graph-matching, landmark-based or skeleton-based pose estimation.

The system according to the present invention may likewise be adapted to estimate or extrapolate a path of movement of the sensor means and/or display means based on image data acquired previously, and may be further adapted to employ this estimate to assist in the registration of subsequent images. By combining a fine-grained estimation as described above with an estimate or extrapolation of the movement of the sensor means and/or display means, the accuracy and speed of the fine-grained pose estimation may be significantly enhanced.

The system according to the present invention may likewise be employed to assist in image-guided interventions, for instance when positioning medical instruments relative to anatomical structures.

According to a preferred embodiment, the sensor means is adapted to sense an object to be placed at a predetermined pose relative to said subject and/or to be moved along a predetermined trajectory relative to said subject, wherein said visualization means comprise guiding means for generating and displaying on said display means an image allowing a user to assess to which extent a pose and/or movement of said object coincides with said predetermined pose or trajectory, respectively.

The object may be an instrument such as a medical or surgical instrument, or any other kind of object that shall be placed at a predetermined position relative to said subject and/or shall be moved along a predetermined trajectory relative to said subject. Said position may be a position above or besides a surface of said subject, or may be a position in the interior of said subject. In the same way, said trajectory may be a trajectory extending above or besides the surface of said subject, or may extend partly in or through said subject. In particular, said trajectory may extend partly externally and partly internally with respect to said subject. For instance, said trajectory may be an insertion path such as a predetermined path along which a physician may want to insert a needle through the surface of the patient and to move the tip of said needle to a predetermined body part. The position of the surface relative to the anatomical structures may vary over time, such as if a patient breathes while being examined. The visualization means may be adapted to monitor, display and/or compensate this surface movement.

Said image may be any image allowing a user to assess to which extent a pose and/or movement of said object coincides with a predetermined pose or trajectory, respectively. In particular, said image may comprise an indication of said pose and/or said predetermined trajectory. The image may further comprise an image of said surface of said subject and/or said object and/or said anatomical data relating to said subject.

Said object may be sensed by determining a distance of said sensor means to at least of a part of a surface of said object.

Said guiding means may then be further adapted to determine said pose of said instrument relative to the predetermined pose or trajectory, and to provide directions for the user how to move said object to said predetermined pose or along said predetermined trajectory, respectively.

Alternatively, said object may be sensed simply by recording a physical image of said object.

In a preferred embodiment, said anatomical data comprises said predetermined pose and/or said predetermined trajectory of said object.

This embodiment allows to plan a predetermined trajectory, such as an insertion path for inserting a needle into the patient. Employing the pre-recorded medical image data, a physician may choose a path from a skin entry point to a tumor to be treated. The predetermined trajectory may then be displayed on the display means alongside the medical image data and an intensity image of the surface of the patient and the medical instrument. The physician may align the instrument with the trajectory, and may move the instrument along the trajectory from the skin-entry point to the tumor. This allows the medical instrument to be inserted with a high level of accuracy, and reduces the risk of damage to the surrounding body parts or tissue. No external tracking of the object is required.

A single sensor means, such as a single time-of-flight camera, may be sufficient to sense a distance from said sensor means to said surface of said subject, and to sense said object. Said sensor means may be a camera adapted to provide both a range image and a physical image, such as an intensity image.

In a preferred embodiment, said sensor means is adapted to record a physical image of said surface of said subject and/or of said object, in particular an intensity image of said surface of said subject and/or of said object, wherein said display means are adapted to display said physical image.

Said sensor means may employ stereoscopy, structured light, passive monocular techniques and/or simultaneous localization and mapping (SLAM). Stereoscopy and structured light are particularly preferred.

Preferably, said guiding means are adapted to generate and display on said display means a representation of said object corresponding to said predetermined pose and/or said predetermined trajectory. Said representation may preferably overlie or underlie said physical image.

The representation of said object may be any 3-dimensional or 2-dimensional representation of said object. In particular, said representation may be a projected shape of said object.

Said representation may indicate the predetermined pose and/or the predetermined trajectory. Hence, the user can move the object to a predetermined pose or follow the predetermined trajectory simply by aligning the object with its representation.

The present invention likewise relates to a method for visualizing anatomical data, comprising the steps of sensing a distance between a sensor means and at least a part of a surface of a subject to be examined, determining a position and/or an orientation of said sensor means and/or a display means relative to said surface of said subject by evaluating distance information acquired in said sensing step, and visualizing anatomical data relating to said subject on said display means in accordance with said position and/or orientation of said sensor means and/or display means.

Said sensor means may be a sensor means with some or all of the features indicated above. Likewise, said display means may be a display means with some or all of the features as described above. In particular, said sensor means may be portable, and said display means may likewise be portable and may be attached to said sensor means.

Preferably, the method according to the present invention may also comprise the step of sensing intensity information alongside said distance information.

According to an embodiment of the present invention, the method may further comprise a step of sensing a distance between said sensor means and said display means.

According to a preferred embodiment, anatomical data relating to said subject may be visualized on said display means at a position on said display means in accordance with a position of an anatomical feature of said subject to be examined as seen from a direction and/or from a distance that correspond to a direction and/or a distance between said subject and said sensor means, or a direction and/or a distance between said subject and said display means.

In a preferred embodiment, said anatomical data relating to said subject is visualized on said display means as seen from a direction and/or from a distance that correspond to a direction and/or a distance between said subject and said sensor means, or a direction and/or a distance between said subject and said display means. In particular, anatomical data relating to an internal structure of said subject, for instance a body part, may be visualized in said display means as seen from a direction and/or from a distance that correspond to a direction and/or a distance between said internal structure of said subject and said sensor means, or a direction and/or a distance between said internal structure of said subject and said display means.

The method according to the present invention may further comprise a step of recording a physical image of said surface of said subject, and displaying said surface image together with anatomical data relating to at least a part of said surface. Preferably, said surface image may be displayed together with anatomical data relating to an internal structure lying underneath at least a part of said surface.

According to a preferred embodiment, the method may further comprise the steps of generating from said distance information a first surface profile of at least a part of a surface of said subject, and comparing said first surface profile against a second surface profile generated from said anatomical data. Comparing said first surface profile against said second surface profile may be performed by means of graph-matching.

Alternatively or additionally, a skeleton model may be generated from said distance information and/or intensity information acquired in said sensing step, and may be compared against said anatomical data.

Alternatively or additionally, the method according to the present invention may further comprise the steps of identifying a first plurality of landmarks from said distance information and/or from intensity information acquired in said sensing step, identifying a second plurality of landmarks from said anatomical data, and determining said position and/or orientation of said sensor means and/or display means by matching said first plurality of landmarks to said second plurality of landmarks.

A method according to the present invention may also comprise the steps of generating from said distance information and/or intensity information acquired at a first point in time a first estimate of said position and/or said orientation of said sensor means (26) and/or said display means (22) by comparing said distance information and/or intensity information against said anatomical data, and subsequently generating a second estimate of said position and/or said orientation by evaluating said first estimate and comparing said distance information and/or intensity information against distance information and/or intensity information acquired at a second point in time, said second point in time later than said first point in time.

In a method according to the present invention, said step of determining said position and/or orientation of said sensor means and/or said display means may preferably comprise the steps of generating a surface profile of at least part of said surface of said subject from said distance information and/or from intensity information, comparing said surface profile against said anatomical data, and computing an affine transformation that aligns said anatomical data with said surface profile.

Said affine transformation may be a rotation and/or a scaling and/or a linear shift operation. In particular, said affine transformation may be a rigid transformation.

Alternatively or additionally, said step of determining said position and/or orientation of said sensor means and/or display means may comprise the steps of selecting a plurality of features in a first image generated from said distance information and/or from intensity information, identifying the positions of said features in said first image, and identifying at least a part of said plurality of features and their respective positions in a second image generated from said distance information and/or from intensity information.

The method according to the latter embodiment may further comprise the steps of determining, from the relative change in the position of said features, the corresponding change in the position and/or orientation of said sensor means and/or said display means, and updating said position and/or orientation of said portable sensor means and/or display means accordingly.

Additionally or alternatively, said step of determining said position and/or orientation of said sensor means and/or said display means may comprise the steps of simulating a first range image based on said anatomical data, and comparing said simulated first range image against a second range image generated from said distance information.

According to a preferred embodiment, the method further comprises a step of sensing an object to be placed at a predetermined pose relative to said subject and/or to be moved along a predetermined trajectory relative to said subject, wherein said step of visualizing comprises a step of generating and displaying on said display means an image allowing a user to assess to which extent a pose and/or movement of said object coincides with said predetermined pose or trajectory, respectively.

Preferably, said anatomical data comprises said predetermined pose and/or said predetermined trajectory of said object.

According to a preferred embodiment, the method further comprises the steps of recording a physical image of said surface of said subject and/or of said object, in particular an intensity image of said surface of said subject and/or of said object, displaying said physical image on said display means, and generating and displaying on said display means a representation of said object corresponding to said predetermined pose and/or said predetermined trajectory.

Said representation may overlie said physical image.

In a preferred embodiment, said representation is a projected shape of said object.

Visualization by means of camera-based methods constitutes an independent aspect of the present invention. A system for visualizing anatomical data according to this latter aspect comprises a display means, a camera means adapted to record an image of at least a part of a surface of a subject to be examined, and a position tracking means adapted to determine a position and/or orientation of said camera means and/or said display means relative to said surface of said subject by means of three-dimensional surface reconstruction, and/or by means of identifying and tracking a plurality of image features in consecutive images provided by said camera means. Said system further comprises a visualization means adapted to visualize on said display means information generated from anatomical data relating to said subject, wherein said visualization means is adapted to visualize said information generated from said anatomical data on said display means in accordance with said position and/or orientation of said camera means and/or said display means.

Said system may preferably employ stereoscopy or structure from motion to generate information about said surface of said subject to be examined.

Said camera means may comprise an optical camera, or a plurality of optical cameras.

Said system according to the latter independent aspect may comprise one or a plurality of features described above with reference to the system comprising a sensor means instead of a camera means, wherein "camera means" should be substituted for "sensor means" in these embodiments.

BRIEF DESCRIPTION OF THE DRAWINGS

The features and numerous advantages of the present invention will be best understood and appreciated from a detailed description of the accompanying figures, in which FIG. 1 schematically illustrates the use of a system for visualizing medical image data for inspecting the knee joint of a patient, with a blow-up drawing FIG. 1a of the visualization system inserted.

DETAILED DESCRIPTION

Figures 1, 1A:
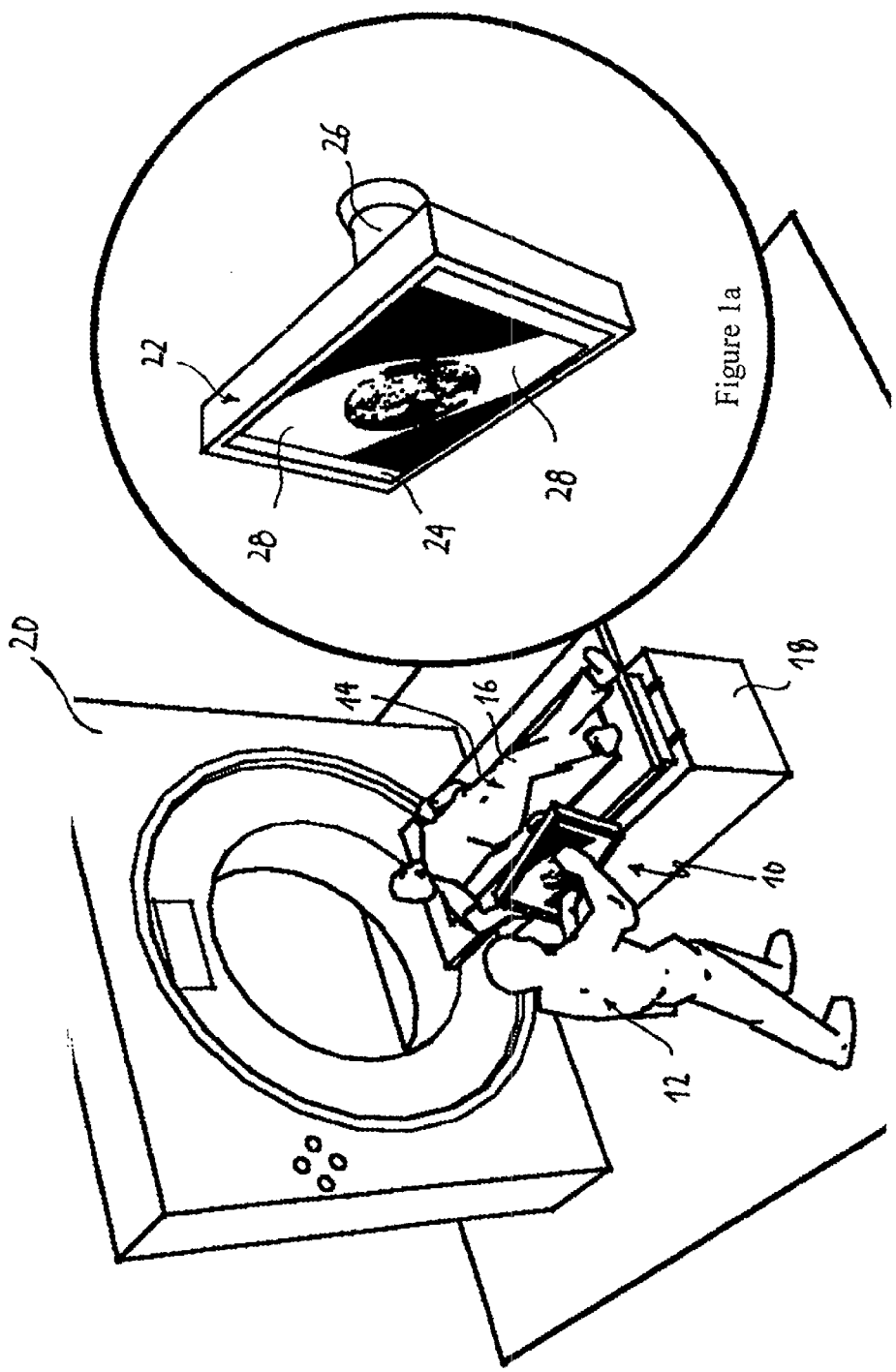

FIG. 1 illustrates a visualization system 10 according to the present invention as used by a physician 12 to examine the knee joint 16 of a patient 14. The patient 14 is drawn resting on a movable table 18 in an examination room equipped with a computed tomography scanner 20. However, this is a mere example, and it is one of the advantages of the present invention that the visualization system 10 can be employed in almost any environment, be it in a hospital or at the patient's home.

The visualization system 10 according to the specific example is illustrated in greater detail in FIG. 1a and comprises a display means 22 equipped with a screen 24. The display means 22 shown in FIG. 1 is a tablet PC, but may alternatively be any other computer device equipped with a screen 24 and suitable for displaying images. Mounted and physically attached to the backside of the display means 22 (opposite to the screen 24) is a time-of-flight camera 26. The time-of-flight camera 26 may alternatively be integrated into the (backside of the) display means 22. The time-of-flight camera 26 serves as a sensor means adapted to generate distance data by means of a time-of-flight measurement. The time-of-flight camera 26 is able to generate dense range images and corresponding grayscale intensity images from a given scene in real-time. Its operation principle is generally similar to that of a laser scanner, with the additional advantage that a whole scene may be captured at once. State of the art time-of-flight cameras provide more than 50 images per second. The range may be illuminated by emitting a light pulse, usually a pulse of infrared light, and the distance data may be generated by measuring the time it takes a light pulse to reach the object and be reflected back into the camera device. Continuous wave modulation instead of pulse modulation may likewise be employed. In the latter approach, a cosine-shaped modulated light signal near the infrared spectral range may be emitted by the time-of-flight camera 26, and may be reflected by the objects to be observed. Based on the knowledge of the speed of light and the modulation frequency, the distance can be computed from the phase shift between the emitted and the reflected light signal.

Optionally, the visualization system 10 also comprises a conventional colour camera (not shown) to provide high resolution colour images of the scene. The colour camera can be calibrated with the time-of-flight camera and can be attached alongside the time-of-flight camera 26 to the backside of the display means 22, or can equally well be integrated into the backside of the housing of the display means 22.

The visualization system 10 can be employed for on-patient visualization of pre-recorded medical images, such as the medical images provided by the computed tomography scanner 20, or any other medical imaging device suitable for acquiring static 3D images, such as a magnetic resonance imaging (MRI) scanner. Preferably, the medical imaging modality is chosen such that it provides surface information alongside information pertaining to the internal structures of the patient, e.g. a computer tomography scanner or a magnetic resonance imaging scanner. The medical image data may be acquired beforehand and may be recorded and stored, e.g. in the Picture Archiving and Communications System (PACS) of a hospital, from which they may be accessed by the visualization system 10.

The visualization system 10 further comprises a visualization means equipped with a graphic processing unit and with medical image processing software to segment the skin as well as all other structures of interest. The visualization means may be integrated into the tablet PC 22. Alternatively, the computations may be performed remotely on an external server.

In any case, the dimensions of the display means 22 and time-of-flight camera 26 are such that the combined device is small and lightweight enough to be portable. The physician 12 may then move the display means 22 freely along the body of the patient 14 with the mounted time-of-flight camera 26 pointing in the viewing direction of the user, as illustrated in FIG. 1.

Figure 2:
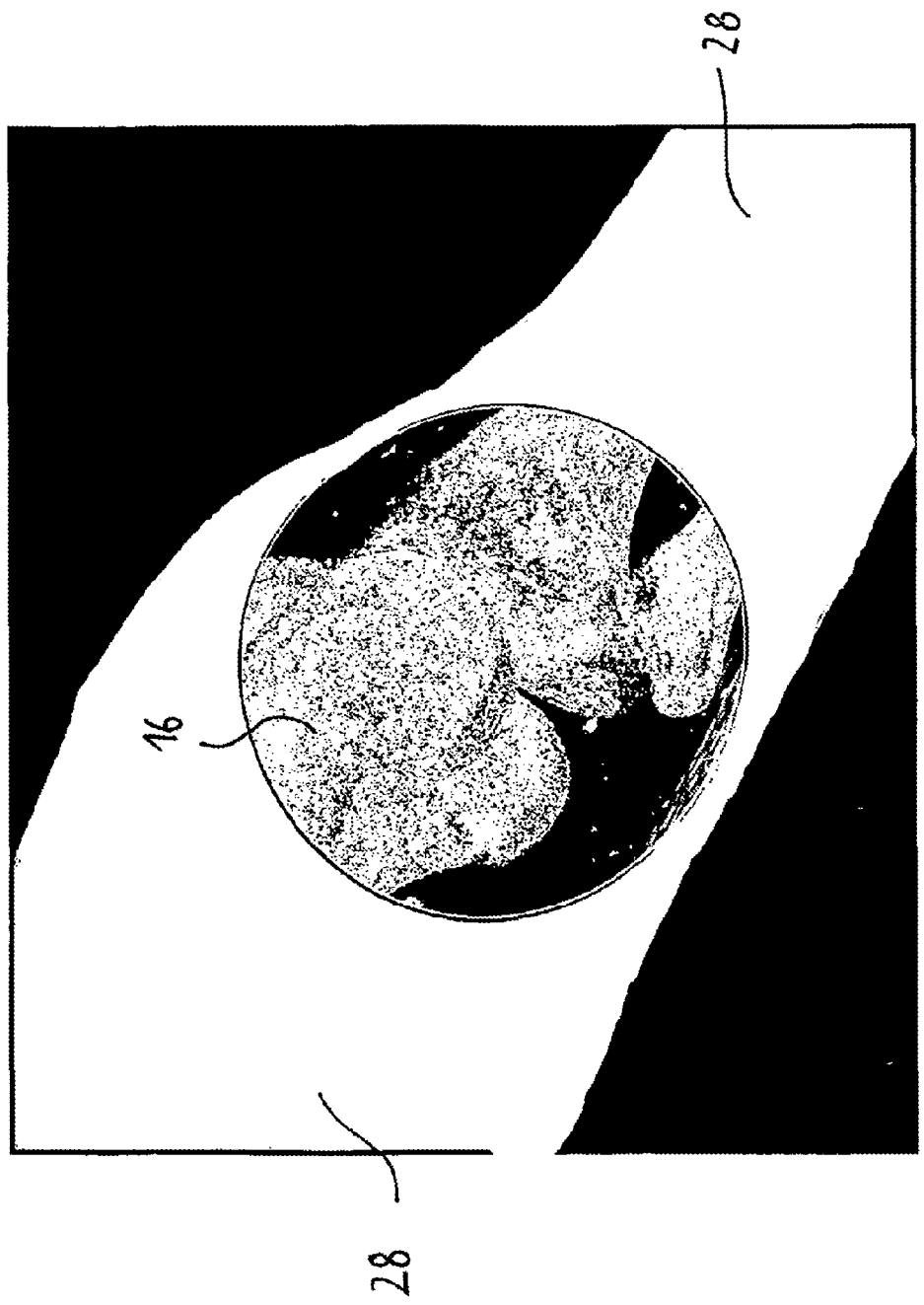
FIG. 2 schematically illustrates a surface rendering of the medical image data of the patient's knee joint on a display means according to the present invention, wherein the medical image of the knee joint is superimposed with a surface image masking neighbouring body parts.

By evaluating the distance information provided by the time-of-flight camera 26, the pose of the time-of-flight camera 26 relative to the surface of the patient 14 may be tracked and may be continuously updated to follow the movements of the display means 22 along the body of the patient 14. In the sense of the present invention, pose may mean position and orientation. Once the viewing direction of the physician 12 relative to the patient 14 is known, the visualization means may set the virtual camera showing the 3D medical image data in accordance with the pose of the time-of-flight camera 26. By looking onto the screen 24, the physician 12 hence obtains a kind of "x-ray vision" into the patient, as illustrated in FIG. 2.

Once the time-of-flight camera 26 has been initialized and calibrated, the visualization of medical image data with the visualization system 10 as shown in FIG. 1 may proceed in three consecutive steps: (i) pre-processing of the camera data, (ii) camera pose estimation, and (iii) visualization. These steps may be iteratively repeated as the camera pose changes during movement along the surface of the patient 14.

(i) Pre-Processing

After distortion correction based on a standard calibration procedure for the intrinsic camera parameters as known from the state-of-the-art, the range image may be denoised using a variant of a bilateral filter that takes into account the intensity and distance measured in the individual pixels. Next, a threshold filter may be applied to the distance image to segment those parts of the image that correspond to the surface of the patient 14. Finally, a surface image may be generated by converting the range image into Cartesian coordinates and applying a Delaunay-based triangulation method. Pre-processing may likewise involve an identification of those parts of the range image that correspond to the surface of the patient 14.

(ii) Camera Pose Estimation

For each image frame, the pose of the time-of-flight camera 26 relative to the surface of the patient 14 may be estimated as follows: Initially, i.e. upon start of the visualization method, a graph-based registration process may be performed to obtain an initial alignment of the surface profile generated from the range image with a surface profile generated from the pre-recorded medical image data. This may be achieved by employing a graph-matching algorithm as described in T. R. dos Santos et al., "Correspondence Search for Surface-Based Intra-Operative Registration", in T. Jiang et al., "Medical Image Computing and Computer-Assisted Intervention—MICCAI 2010, Lecture Notes in Computer Science, Vol. 6362, Springer 2010, p. 660.

Alternatively or additionally, an initial alignment may also be found by means of a landmark-based pose estimation. This can be achieved by identifying a plurality of characteristic landmarks in the range image and/or intensity image provided by the time-of-flight camera 26, or in a video image provided by the (optional) conventional colour camera. Any prominent or characteristic feature found in an image may serve as a landmark, such as a steep gradient in a range or intensity image, or a colour gradient in a video image. Corresponding landmarks may be identified from the medical image data, and the landmarks may be matched to identify the pose of the time-of-flight camera 26 with respect to the surface of the patient 14. Preferably, landmarks identified from the acquired camera images may be natural landmarks, e.g. landmarks found in the topology of the subject to be examined. These may be joints linking the limbs of the patient 14, or orifices of the body of the patient 14. However, alternatively or additionally, artificial landmarks such as markers may also be used. These markers may be attached to the subject to be examined at predetermined positions, and may assist in the initial camera pose estimation.

Alternatively or additionally, an initial pose estimate may also be achieved based on a skeleton model. The contour of the patient 14 may be identified and used to generate a skeleton graph representing said patient 14. In such a skeleton graph, edges may represent the limbs of the patient 14, and nodes may represent the joints connecting the limps. The skeleton model may then be compared against the pre-recorded medical image data to derive a rough estimate of the initial camera pose. This technique may be very suitable to accommodate changes in the relative positioning of the limbs, and hence may account for movements of the patient 14 during examination.

All these techniques have the advantage that they do not rely on a previous estimate of the camera pose, and are hence very suitable for initial pose estimation. Subsequently, they may be applied whenever the camera pose of the time-of-flight camera 26 is changed, or only as needed if fine registration techniques are insufficient to account for updates of the camera pose.

Once a rough pose estimate has been found, at least one of the following fine registration techniques may be applied to determine the camera pose with enhanced precision. These techniques may rely on the initial pose estimate acquired previously, and may allow a continuous update of the camera pose:

Point-based registration: Based on the knowledge of the camera parameters, a surface profile may be generated from the range image and/or intensity image of the time-of-flight camera 26. A further surface profile may be extracted from the 3D medical data set. Both the surface profile generated from the time-of-flight camera 26 and the surface profile extracted from the 3D medical data set may be converted into point clouds. Next, a variant of the Iterative Closest Point (ICP) algorithm may be applied to align the surfaces. The algorithm iteratively (1) establishes point correspondences given the current alignment of the data, and (2) computes a rigid transformation that aligns the surface profile generated from the pre-recorded medical image data with the surface profile generated from the range image. The algorithm proposed in L. Maier-Hein et al., "Accounting for Anisotropic Noise in Fine Registration of Time-of-Flight Range Data with High-Resolution Surface Data", in T. Jiang et al., "Medical Image Computing in a Computer-Assisted Intervention—MICCAI, Lecture Notes in Computer Science, Vol. 6361, Springer 2010, p. 251, is particularly suitable for this purpose in that it may account for the high noise along the viewing direction of the time-of-flight camera 26. It may be sufficient and appropriate to select a suitable subset of data points, which allows for particularly fast computing.

Feature-based registration: Alternatively or additionally, an automatic feature tracking algorithm may be applied to detect and track features automatically in consecutive images. Given an image pair, those features that are present in both images and have similar feature descriptors may be assumed to correspond to the same anatomical location. The descriptors may be based on the surface profile generated from the range data only. Alternatively or additionally, the descriptors may also be based on the intensity image provided by the time-of-flight camera 26, or on a colour image provided by the optical camera (not shown) mounted to the display means 22 alongside the time-of-flight camera 26. A point-based registration may then be applied to align the surfaces using at least three feature points. For this purpose, the Cartesian coordinates of the feature points may be extracted from the corresponding image. To account for the high noise along the viewing direction of the camera, an anisotropic point registration can be applied. It is also possible to give different weights to corresponding features depending on the degree of similarity in consecutive images. Due to the initial registration with the static surface profile generated from the 3D medical data set and the registration of any two consecutive time-of-flight images, each time-of-flight-image can be registered to the pre-recorded medical image data to obtain the current pose of the time-of-flight camera 26 when the time-of-flight camera 26 is moved along the body of the patient 14.

Simulation-based registration: Alternatively or additionally, the parameters representing the camera pose (e.g., three Cartesian coordinates defining a location and three Euler angles defining an orientation) can be optimized by means of an evolutionary algorithm. For this purpose, a cost function depending on the pose parameters may be defined to quantify the difference between the required true range image and a simulated range image that is computed for the camera pose represented by the given parameters. The range images may be simulated by generating a ray that represents the direction of light for each time-of-flight pixel. The distance value may then be determined by finding a first intersection of the ray with one of the surface meshes in the 3D medical data set. During the optimization, the pose parameters may be continuously modified stochastically until a fixed number of iterations has been reached. The parameters corresponding to the best similarity value may then represent the current camera pose, so that the image displayed on the screen 24 may be updated when the time-of-flight camera 26 is moved along the body of the patient 14.

In each time step, the result of the fine registration method may be used to derive the current camera pose and to give an estimate for the camera pose in the next time frame using an extended Kalman filter. Any other technique for predicting and extrapolating the movement of the time-of-flight camera 26 or screen 24 along the surface of a patient may likewise be employed.

The same techniques for predicting or extrapolating the movement of the sensor means and/or display means may likewise be employed to assist in the point-based registration and in the feature-based registration.

(iii) Visualization

As best seen from the inserted blow-up FIG. 1*a* and the enlarged illustration of FIG. 2, the display means 22 may depict a volume rendering of the knee joint 16 of the patient 14. In this example, the 3D medical image is superimposed with a real image of the surrounding skin 28 of the patient's leg, as provided by the optical camera (not shown) mounted to the display means 22 alongside the time-of-flight camera 26. This helps the physician 12 to better assess the position of the features of interest in the 3D medical image data in relation to the surrounding surface structure, e.g. in surgical planning or for better orientation during interventional therapy. The surrounding skin structure may also be extracted from the 3D medical image data, such as from a CT scan. In this case, an optical camera may not be required.

Visualization of pre-recorded medical image data may mean the generation of an image from at least a part of said pre-recorded medical image data. Said image may correspond to a slice view through a body part lying underneath the surface, or rendering of the surface of said body part lying underneath said surface, or any other conventional technique for processing medical data for display on a display means.

The superimposed image shown in FIG. 1*a* and FIG. 2 may be achieved by virtually cutting a sphere-shaped hole into the skin surface. To avoid manipulation of the skin surface mesh for dynamic scenes, the cutting may be realized in display space during the rendering process employing a programmable graphics pipeline, i.e. by utilizing a shading language program that discards pixels of the surface occluding the region of interest.

A volume rendering may be achieved by employing a user-defined transfer function which assigns a colour value as well as an opacity value to each greyscale value of the static 3D image.

However, this is a mere example, and other visualization modes for rendering internal structures may be employed.

For example, in surface rendering previously segmented anatomical structures with assigned colour and opacity values may be rendered as surfaces.

A virtual x-ray image generated based on the current camera pose may likewise be provided.

In a slice view, the pose of the time-of-flight camera 26 may be used to reconstruct an image slice whose normal direction is given by the viewing direction of the time-of-flight camera 26, and whose depth is derived from the proximity of the camera 26 to the patient's surface.

If medical image data of several consecutive layers of the body part under inspection are available, the layer on display may, for instance, be chosen in accordance with the distance of the sensor means and/or display means to the surface of the patient 14. For instance, by moving the time-of-flight camera 26 closer to the surface of the patient 14, the visualization means may be adapted to display deeper layers of the body part. Layers closer to the surface may be displayed when the camera is moved away from the surface. The layers on display may be layers that are orthogonal to a viewing direction of the time-of-flight camera with respect to the surface, or may be any other layer structure for which medical image data is available.

In the configuration shown in FIG. 1, the time-of-flight camera 26 may send the acquired time-of-flight data to the tablet computer 22 serving as display means, to which the time-of-flight camera 26 may be connected via a USB connection. The tablet computer 22 may employ a wireless connection to forward the time-of-flight data to a remote personal computer. Time-of-flight data may be compressed as needed. The remote personal computer stores or has access to the pre-recorded medical image data, and serves as a position tracking means to determine the pose of the time-of-flight camera 26 relative to the surface of the patient 14, either by applying a surface-based registration, a feature-based registration, or a simulation-based registration as described above, or any other suitable technique.

Determining the pose of the camera 26 may comprise the determination of a triple of spatial coordinates (x, y, z) which uniquely define a location of the time-of-flight camera 26 in a three-dimensional coordinate system, as well as a triple of Euler angles ($\alpha$, $\beta$, $\gamma$) that specify an orientation of the time-of-flight camera 26.

Once the pose of the camera have been determined, the spatial and angular coordinates may be sent back to the tablet PC 22 over the wireless connection. The tablet PC 22 may then serve as a visualization means to render the scene in accordance with the current pose of the time-of-flight camera 26.

In the example described above, the portable sensor means, the display means, and the visualization means hence form a portable unit, and are spatially separated from the position tracking means located in the remote PC. However, this is a mere example, and the invention may likewise be practiced in a configuration in which the portable sensor means, the position tracking means, the display means, and the visualization means are all combined into a single portable unit. Alternatively, the portable unit may comprise only the portable sensor means and the display means, whereas both the position tracking means and the visualization means are remotely located, and may communicate with the portable unit over a wireless connection.

In the example described above with reference to FIG. 1, the sensor means 26 is attached to the display means 22. However, in some applications it may be more appropriate to spatially separate the display means 22 from the sensor means 26. For instance, for anatomy teaching the medical image data may be better visualized on the screen of a classroom or lecture theatre, whereas only the portable sensor means is moved along the body of the patient to be examined.

The display may also be any type of 3D display, such as a head-mounted display.

In addition to the 3D medical image data, the anatomical data may also comprise meta-information such as anatomical labels. For instance, these labels may display the name of an anatomical structure seen on the screen 24 of the display means 22, or may comprise supplementary information on that structure. Based on the camera pose estimation, such labels may be displayed at a position that corresponds to the position of the corresponding anatomical structure as shown on the screen 24. This may be very helpful for anatomy teaching.

The anatomical data relating to said subject is not limited to pre-recorded medical data of said subject itself, but may also be some generic medical data, such as information extracted from an anatomy atlas. The relevant anatomical structures derived from said atlas may be registered with the image acquired from the time-of-flight camera, and may hence be displayed at a position where the corresponding structure is to be expected in the patient 14. The anatomical data may also comprise images of anatomical abnormalities, and it may be a student's task to correctly identify these abnormalities when examining the subject with the system according to the present invention.

Information generated from anatomical data may likewise be an insertion path, for instance a predetermined path along which a physician may want to insert a needle through the surface of the patient to a predetermined body part. This path may be visualized on the display means together with some pre-recorded medical image data, and/or together with a physical image of the surface structure of the patient.

The insertion path may be constructed and planned offline, based on previously acquired 3D medical data image, such as data generated from a CT or MRI scan. Once this has been achieved, the final planning may then conveniently be made directly on patient by use of the system and method according to the present invention. An insertion instrument, such as a needle, may additionally be tracked, and its position and/or orientation may then likewise be visualized on the display means.

Figure 3:
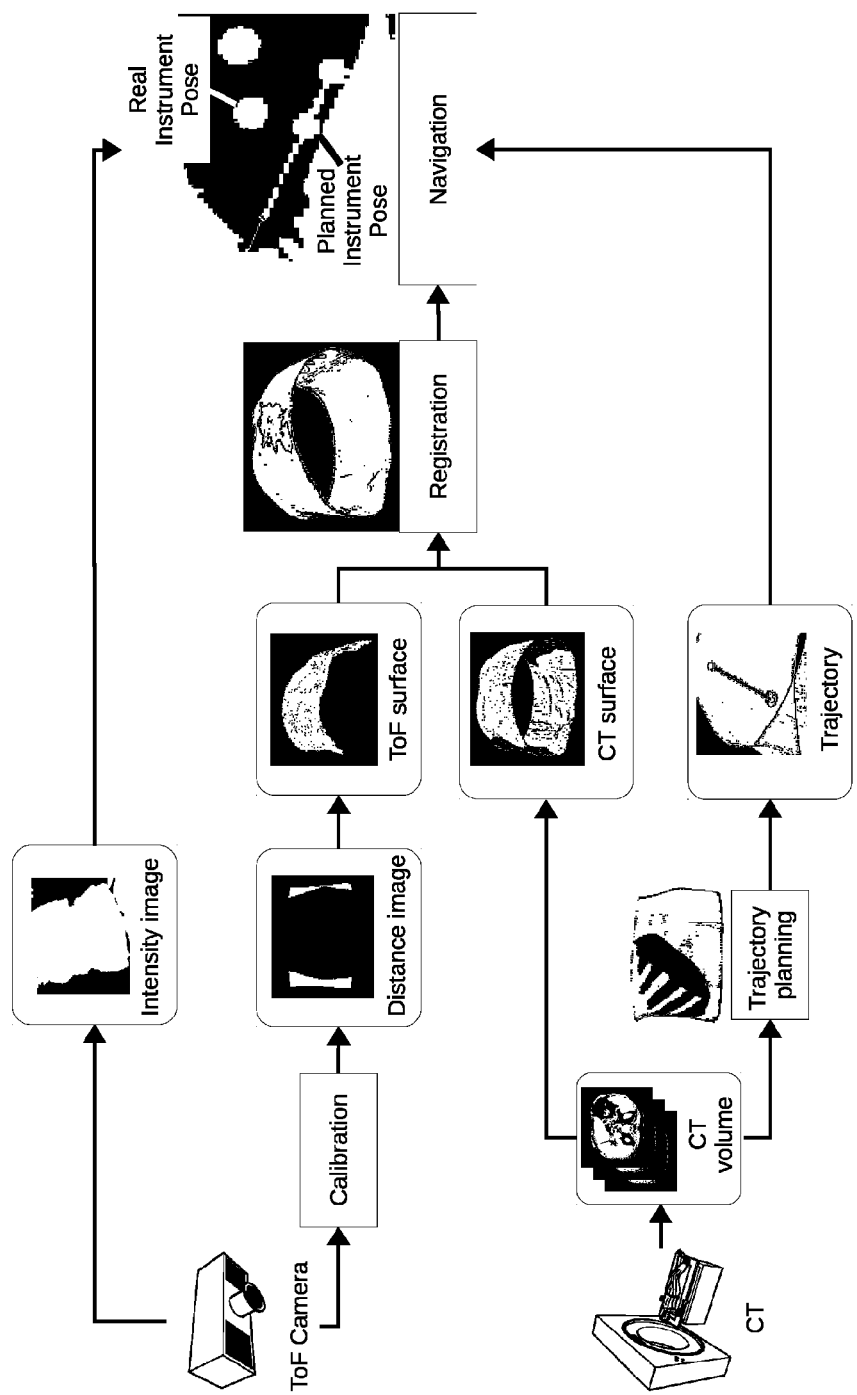
FIG. 3 is a schematic diagram illustrating a workflow of an image-guided intervention according to an embodiment of the present invention.

A workflow for an image-guided intervention in which a medical instrument is moved along a predetermined insertion path is illustrated schematically in FIG. 3. This Figure relates to the specific example of a navigated needle insertion for performing a computer-assisted biopsy or a radiofrequency ablation. However, the invention is not so limited, and may be employed whenever an object, in particular a medical instrument, is to be placed at a predetermined position and/or moved along a predetermined trajectory relative to the patient's surface and/or anatomy. Applications of this type are described in the related application US 2010/0076305A1, but using standard tracking systems. Such tracking systems typically require a lot of hardware, which may impose restrictions on the clinical workflow and may be difficult to employ in an operating theatre.

The present invention allows to overcome these restrictions. The image-guided intervention according to the present invention does not require an external tracking system, but can be implemented with a single camera system comprising a time-of-flight camera equipped with or augmented by an optical camera. Most time-of-flight cameras provide grayscale intensity images corresponding to said range images. The single camera system can be used for (1) registration of the anatomy of the patient with 3D-planning data sets, (2) augmented reality visualization of anatomical data, and (3) instrument guidance. As no bulky equipment is involved, the invention can be easily integrated into the clinical workflow. It is also less expensive and easier to use than conventional systems employing external tracking systems, such as optical or electromagnetic systems.

The hardware components associated with the embodiment are typically a personal computer with a guidance monitor and a camera that a allows for capturing 2D-intensity images, such as RGB images, and corresponding range images. For instance, the camera may be a time-of-flight camera or a structured light camera, such as the Kinect camera available from Microsoft Corporation.

The workflow illustrated in FIG. 3 proceeds in three consecutive steps:

(1) Planning Employing pre-recorded medical image data, such as data from a CT-scan, the physician may select a path from a skin entry point to a predetermined target point, such as a tumor to be treated.

(2) Registration: To register the 3D-planning image to the patient, the 3D-range camera may be used to acquire a surface representing the patient's skin above the target region. This surface information is matched to the corresponding surface extracted from the 3D medical image data, as described above. This registration yields the pose of critical structures and other relevant planning data, such as the needle trajectory, relative to the intra-interventionally acquired surface. After the registration, the position of the planned path relative to the intra-interventionally acquired surface is known. The diving means may be employed to determine whether the image of the instrument as acquired by the sensing means coincides with the projected shape or free the representation of said instrument, and may guide the user to align the instrument with its representation.

(3) Guidance: To transfer the planned path to the patient, the physician may follow an augmented reality (AR) view on the guidance monitor. In the intensity image of the camera, he may see the true instrument pose as well as a projected (virtual) second pose that represents a desired pose prior to needle insertion. The task of the physician is to align the instrument with this projection. For this purpose, he may initially position the tip of the needle at the planned insertion point, which is likewise visualized in the intensity image. Holding the tip of the needle in a constant position, he then starts pivoting the needle until the instrument is finally aligned with the projection, indicating that the needle is now pointing in the correct direction. He may then advance the needle until the desired depth has been reached, as shown by the guidance monitor.

Guiding may be facilitated if the sensor means track the instrument by sensing a distance of the sensor means to said instrument. In this case, the guiding means may directly compare the true pose of the instrument with the predetermine pose and/or planned trajectory, and may guide the user to bring them into correspondence.

Rather than projecting the shape of the instrument into the intensity image of the camera, a 3D representation of the instrument may likewise be displayed.

The registration compensate movement of the surface, such as may be caused by breathing, in order to provide a corrected indication of the relative position of the instrument with respect to the anatomical structure. This may compensate for the change of the needle trajectory relative to a patient's skin depending on the breathing state.

The medical instrument may also be equipped with additional markers that may simplify the sensing of the instrument. The instrument may also be formed in a shape that simplifies the sensing of the instrument by means of the sensing means. For instance, a needle may be equipped with a small crossbeam at a predetermined position. The crossbeam can be positioned such that it does not interfere with the insertion, but allows the sensing means to reliably detect the position and orientation of the needle with respect to the patient surface.

As a variation of the method described with reference to FIG. 3, the trajectory may not necessarily be planned beforehand by employing the medical image data. It may likewise be feasible to plan the trajectory by directly employing the image acquired from said sensor means. For instance, a physician may determine the position of a target directly at the patient, for instance by means of palpation of the patient, and may then select the desired trajectory based on the image data provided by the sensor means, without any reference to pre-recorded image data.

The subject under investigation need not necessarily be a (human or animal) patient, but may likewise be a doll or a skeleton. In such applications, the anatomical data may comprise anatomical labels as described above, and/or medical image data generated from an anatomical atlas. By rendering the anatomical data with the data provided by the sensor means, the labels and/or images may be displayed on the screen 24 in accordance with the camera pose. These applications may likewise prove helpful for anatomy teaching, and students may be required to find and identify pre-defined medical structures by moving the sensor means and/or display means to the corresponding position at the doll or skeleton.

Compared to conventional visualization techniques, the system and method according to the present invention offers several major advantages. In particular, it is markerless, involves no bulky equipment, provides an intuitive mechanism for navigating through a 3D medical data set, and poses no restrictions on the image acquisition. The invention can hence be employed for an improved intervention planning, anatomy teaching, and various other applications that require intuitive visualization of 3D medical data.

The specific embodiments described above and the figures merely serve to illustrate the invention, but are not intended to imply any limitation. The scope of the invention is to be determined solely by the appended set of claims.

The invention claimed is:

1. A system for visualizing anatomical data, comprising:
a display means;
a sensor means adapted to sense a distance of said sensor means to at least a part of a surface of a subject to be examined;
a position tracking means adapted to determine a position and/or an orientation of said sensor means and/or said display means relative to said surface of said subject by evaluating distance information provided by said sensor means; and
a visualization means adapted to visualize on said display means information generated from anatomical data relating to said subject;
wherein said visualization means is adapted to visualize said information generated from said anatomical data on said display means in accordance with said position and/or orientation of said sensor means and/or said display means; and
wherein said position tracking means simulates a plurality of range images based on said anatomical data, and compares said simulated range images against an acquired range image generated from said distance information to identify a simulated range image best corresponding to said acquired range image.

2. The system according to claim 1, wherein said sensor means is adapted to sense a distance of said sensor means to said display means.

3. The system according to claim 1, wherein said sensor means is portable, and wherein said display means is portable and is attached to said sensor means.

4. The system according to claim 1, wherein said sensor means is a time-of-flight camera.

5. The system according to claim 1, wherein said visualization means is adapted to visualize anatomical data relating to said subject on said display means as seen from a direction and/or from a distance that correspond to a direction and/or a distance between said subject and said sensor means, or a direction and/or a distance between said subject and said display means.

6. The system according to claim 1, wherein said sensor means is further adapted to record a physical image of said surface of said subject, and said visualization means is adapted to display said physical image of said surface together with information generated from anatomical data relating to at least a part of said surface.

7. The system according to claim 1, wherein said system is adapted to generate from said distance information a first surface profile of at least a part of said surface of said subject, and further comprises comparison means adapted to compare said first surface profile against a second surface profile generated from said anatomical data.

8. The system according to any of the preceding claims, wherein said sensor means is adapted to sense an object to be placed at a predetermined pose relative to said subject and/or to be moved along a predetermined trajectory relative to said subject, wherein said visualization means comprise guiding means for generating and displaying on said display means an image allowing a user to assess to which extent a pose and/or movement of said object coincides with said predetermined pose or trajectory, respectively.

9. The system according to claim 8, wherein said anatomical data comprises at least one of said predetermined pose and said predetermined trajectory of said object.

10. The system according to claim 8, wherein said sensor means is adapted to record a physical image of said object, wherein said display means are adapted to display said physical image, and wherein said guiding means are adapted to generate and display on said display means a representation of said object corresponding to said predetermined pose and/or said predetermined trajectory.

11. The system according to claim 10, wherein said representation comprises a projected shape of said object or a three-dimensional representation of said object.

12. A method for visualizing anatomical data, comprising the steps of:
sensing a distance between a sensor means and at least a part of a surface of a subject to be examined;
determining a position and/or an orientation of said sensor means and/or a display means relative to said surface of said subject by evaluating distance information acquired in said sensing step; and
visualizing information generated from anatomical data relating to said subject on said display means in accordance with said position and/or orientation of said sensor means and/or display means;
wherein determining said position and/or orientation of said sensor means and/or said display means comprises the steps of simulating a plurality of range images based on said anatomical data, and comparing said simulated range images against an acquired range image generated from said distance information to identify a simulated range image best corresponding to said acquired range image.

13. The method according to claim 12, further comprising the step of sensing a distance between said sensor means and said display means.

14. The method according to claim 12, wherein said anatomical data relating to said subject is visualized on said display means as seen from a direction and/or from a distance that correspond to a direction and/or a distance between said subject and said sensor means, or a direction and/or a distance between said subject and said display means.

15. The method according to claim 12, further comprising the step of recording a physical image of said surface of said subject, and displaying said physical image of said surface together with information generated from anatomical data relating to at least a part of said surface.

16. The method according to claim 12, further comprising the steps of generating from said distance information and/or intensity information acquired at a first point in time a first estimate of said position and/or said orientation of said sensor means and/or said display means by comparing said distance information and/or intensity information against said anatomical data, and subsequently generating a second estimate of said position and/or said orientation by comparing said distance information and/or intensity information from said first point in time against distance information and/or intensity information acquired at a second point in time, said second point in time later than said first point in time.

17. The method according to claim 12, wherein said step of determining said position and/or orientation of said sensor means and/or said display means comprises the steps of generating a surface profile of at least part of said surface of said subject from said distance information and/or from intensity information, comparing said surface profile against said anatomical data, and computing an affine transformation that aligns said anatomical data with said surface profile.

18. The method according to claim 12, wherein said step of determining said position and/or orientation of said sensor means and/or said display means comprises the steps of selecting a plurality of features in a first image generated from said distance information and/or from intensity information, identifying the positions of said features in said first image, and identifying at least a part of said plurality of features and their respective positions in a second image generated from said distance information and/or from intensity information.

19. The method according to claim 12, further comprising a step of sensing an object to be placed at a predetermined pose relative to said subject and/or to be moved along a predetermined trajectory relative to said subject, wherein said step of visualizing comprises a step of generating and displaying on said display means an image allowing a user to assess to which extent a pose and/or movement of said object coincides with said predetermined pose or trajectory, respectively.

20. The method according to claim 19, wherein said anatomical data comprises said predetermined pose and/or said predetermined trajectory of said object.

21. The method according to claim 19, wherein said step of sensing said object comprises the step of recording a physical image of said object, and said method further comprises the step of displaying said physical image on said display means, and generating and displaying on said display means a representation of said object corresponding to said predetermined pose and/or said predetermined trajectory.

22. The method according to claim 21, wherein said representation comprises a projected shape of said object or a three-dimensional representation of said object.

\* \* \* \* \*